United States Patent [19]

Theodoropulos

[11] 4,379,928
[45] Apr. 12, 1983

[54] SYNTHESIS OF AMIDES

[75] Inventor: Spyros Theodoropulos, Yorktown Heights, N.Y.

[73] Assignee: Union Carbide Corporation, Danbury, Conn.

[21] Appl. No.: 240,327

[22] Filed: Mar. 4, 1981

[51] Int. Cl.$^3$ .................. C07C 102/00; C07C 102/04; C07C 102/06

[52] U.S. Cl. .................. 544/176; 260/404; 544/386; 546/245; 560/32; 560/115; 560/163; 564/132; 564/133; 564/134; 564/137; 564/138; 564/139; 564/141; 564/144; 548/530; 548/524; 548/540

[58] Field of Search ............... 564/132, 137, 141, 144, 564/133, 134, 138, 139; 260/404, 326 A; 560/163, 115, 32; 546/245; 544/386, 176

[56] References Cited

U.S. PATENT DOCUMENTS

| | | | |
|---|---|---|---|
| 2,594,044 | 4/1952 | Loder | 196/14.35 |
| 2,801,217 | 7/1957 | Nelson | 252/1 |
| 2,927,128 | 3/1960 | Lindahl et al. | 260/501 |
| 3,417,114 | 12/1968 | Kuceski | 260/404 |
| 3,580,968 | 5/1971 | Kuraishi et al. | 564/137 |
| 3,988,358 | 10/1976 | Heck | 564/132 X |
| 4,224,243 | 9/1980 | Aoyama et al. | 564/132 |
| 4,256,665 | 3/1981 | McEntire | 564/135 |
| 4,256,666 | 3/1981 | McEntire | 564/135 |
| 4,259,259 | 3/1981 | McEntire | 564/137 |
| 4,269,998 | 5/1981 | Inai | 564/132 |

FOREIGN PATENT DOCUMENTS

| | | | |
|---|---|---|---|
| 1146869 | 4/1963 | Fed. Rep. of Germany | 564/132 |
| 1222703 | 2/1971 | United Kingdom . | |
| 223091 | 11/1968 | U.S.S.R. | 564/132 |

*Primary Examiner*—Thomas A. Waltz
*Attorney, Agent, or Firm*—Bernard Francis Crowe

[57] ABSTRACT

Alkyl amides have been synthesized from cyclic anhydrides, carboxyl acids and their esters by contacting them with an amine carbamic acid salt.

19 Claims, No Drawings

SYNTHESIS OF AMIDES

BACKGROUND OF THE INVENTION

This invention pertains to the synthesis of amides using amine carbamic acid salts and more particularly to the use of alkylamine carbamic acid salts as well as aralkylamine carbamic acid salts to effect this end.

Organic amides have found widespread industrial application as solvents and especially as aprotic polar solvents. The long-chain fatty acid amides are currently used as anti-block and anti-slip agents for ethylene polymers and as surfactants. Ethylenically unsaturated dibasic acid amides, particularly maleic acid diamide and fumaric acid diamide are monomers used in various addition and condensation polymerizations. Other diamides have found utility as chelating agents.

Prior art methods of preparing amides have included the acylation of amines, as described by M. L. Bender in Chem. Rev. 60; 53, (1960); "The Chemistry of Amides," by J. Zabiscky, page 75, Interscience Publishers, N.Y.C., (1970); and by J. Hipkin et al., J. Chem. Soc. (B), 345, (1946). This method requires that a carboxylic acid derivative which activates the molecule to react with an amine. Acyl halides, esters and anhydrides have been used as the carboxylic acid derivative as shown below in the respective equations.

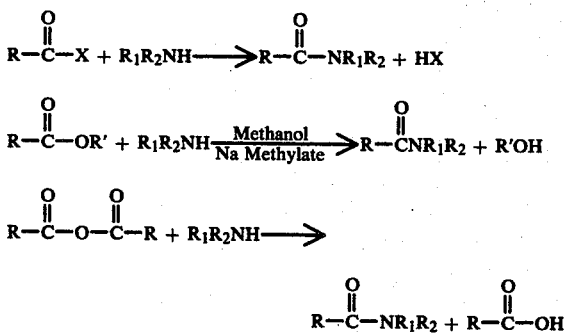

A second prior art means for synthesizing amides is the amination of carboxylic acids described by H. Schindlbauer et al., Synthesis 11, 634 (1962), J. K. Lawson, Jr. et al., J. Org. Chem. 28, 232 (1963), and J. F. Brauzier et al., Bull. Soc. Chim. France (6), 2109 (1966). Several variations of this method are delineated in the following equations.

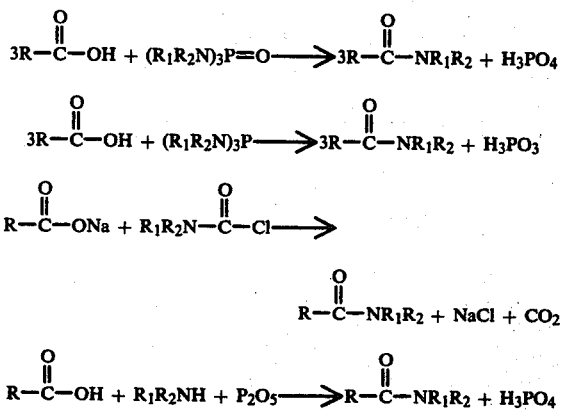

In all of the above equations R, $R_1$, $R_2$ and $R'$ are alkyl groups.

While the above-described methods provide a variety of amides, they exhibit several drawbacks, viz.,:

(1) Require a derivative preparation step.
(2) Require the use of solvents for the reaction.
(3) Generate solid by-products and therefore disposal problems.
(4) Require catalysts, complicated extraction steps and tedious purification steps.

A third method of preparing amides has also been used and is described by E. R. Shephard et al. in J. Org. Chem. 17, 568 (1952). This is a thermal dehydration of the ammonium salt formed by the interaction of a carboxylic acid and an amine as shown below.

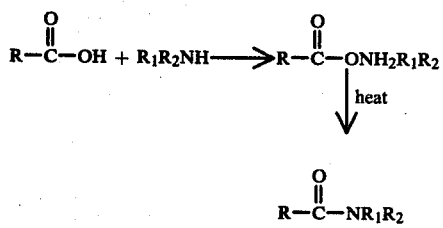

This method suffers the drawbacks of requiring excessive heating at high temperatures and often necessitates the use of metal oxide catalysts. In addition the use of amine reagents tends to affect the unsaturated moieties of carboxylic substrates containing such moieties.

It is therefore an object of this invention to provide an improved process for the preparation of organic amides free of the defects of the prior art techniques.

Other objects will become apparent to those skilled in the art upon a further reading of the specification.

SUMMARY OF THE INVENTION

A method of preparing amides has been discovered which comprises contacting an organic compound containing at least one carboxyl, carboxylic acid ester or carboxylic acid anhydride functionality with an amine carbamic acid salt having the formula:

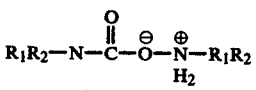

wherein each of $R_1$ and $R_2$ is H, alkyl having 1 to about 20 carbon atoms including linear, branched and cyclic alkyls, aralkyl groups having the formula

where n is an integer having values of 1 to about 5 inclusive, Ar is an aromatic radical having up to about 15 carbons and optionally a hereto atom and the grouping $-N-R_1R_2$ can be piperazine, piperidine, morpholine or or pyrrole radicals, at a temperature of about 25°–250° C. until an amide forms.

The preferred organic compounds are:

(1) carboxylic acid anhydrides having the formula

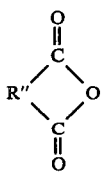

wherein R" is an dialkylene ether or a divalent aliphatic radical having 1 to about 4 carbons, o-phenylene or o-cyclohexylene radicals;

(2) carboxylic acids having the formula

R—COOH wherein R is H, alkyl having 1 to about 20 carbons or —R'—COOH wherein R' is alkylene having 1 to about 18 carbons; and (3) carboxylic acid esters having the formula

R—COOR$_2$ wherein R is as defined above and R$_2$ is alkyl having 1 to about 8 carbons.

Illustrative carboxylic acid anhydrides include:

Diels Alder adducts of maleic anhydride, maleic anhydride, maleic anhydride-olefin reaction products, such as, 2-dodecenyl maleic anhydride, fumaric anhydride, diglycolic anhydride, phthalic anhydride, 2,3-pyridine dicarboxylic acid anhydride, itaconic anhydride, benzene tetracarboxylic acid anhydride, glutaric acid anhydride, succinic anhydride, and the like.

Illustrative organic compounds containing at least one carboxyl include aliphatic acids, such as, formic acid, acetic acid, propionic acid, and the like; saturated fatty acids, such as, butyric acid, isovaleric acid, caproic acid, caprylic acid, capric acid, lauric acid, myristic acid, palmitic acid, stearic acid, arachidic acid, and the like; unsaturated fatty acids, such as, oleic acid, palmitoleic acid, ricinoleic acid, petroselenic acid, vaccenic acid, linoleic acid, linolenic acid, arachidonic acid, and the like; dibasic acids, such as, succinic acid, maleic acid, malonic acid, diglycolic acid, glutaric acid, and the like.

Illustrative carboxylic acid esters include:
methyl formate
ethyl-2-phenoxy acetate
ethyl formate
methyl acetate
ethyl acetate
propyl propionate
butyl acetate
methyl butyrate
ethyl pentanoate
propyl octanoate
ethyl laurate
hexyl acetate
lauryl propionate
octadecyl formate, and the like.

Amine carbamates have been known for almost one hundred years [cf. E. A. Werner, J. Chem. Soc. 117, 1046 (1920)]. However their utilization has been negligible and they have not been used as in the instant invention. The one significant application appears to be their conversion to ureas as shown below.

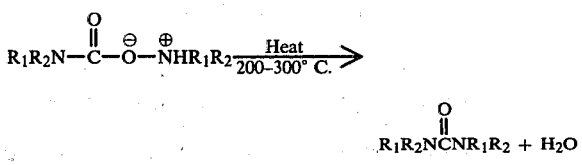

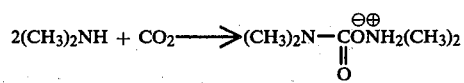

The amine carbamic acid salts can be prepared by the interaction, e.g., of an alkylamine and carbon dioxide. A suitable procedure is described in U.S. Pat. No. 2,927,128 by H. A. Lindahl et al. assignors to Pure Oil Co.

Alternately the amine carbamic acid salts can be generated in situ by the reaction of carbon dioxide with an amine. In the simple case where the amine is dimethyl amine, the equation for the reaction is:

$$2(CH_3)_2NH + CO_2 \longrightarrow (CH_3)_2N\overset{\ominus\oplus}{\underset{\underset{O}{\parallel}}{-}}CONH_2(CH_3)_2$$

The organic compound containing a carboxyl group or derivative thereof can then be added to the dimethyl amine carbamate formed in situ and the preparation of the dimethyl amide carried out in this fashion. The dimethylamine carbamate serves as an active dialkylamine carrier and as a polar solvent.

Suitable dialkylamines include dimethylamine, diethylamine, dipropylamine, dibutylamine, dihexylamine, piperazine, morpholine, pyrrolidine, piperidine, and the like.

Suitable monoalkylamines include methylamine, ethylamine, propylamine, N-aminoethyl morpholine, and the like.

Suitable aromatic radicals in aralkyl groups having the formula Ar-(-CH-)$_2$ include phenyl, naphthyl, thienyl, furyl, pyrryl, and like radicals.

Although temperatures ranging from ambient to over 250° C. can be used to effect the amidation reaction, it is preferred to use a range of about 50° to about 200° C.

Pressure is not narrowly critical. For economic reasons atmospheric pressure is preferred where feasible. For volatile substrates superatmospheric pressures serve best. If desired even subatmospheric pressures can be used.

The simplicity and specificity of the amidation reaction of this invention is evinced by the fact that the products are water and carbon dioxide.

The process can be practiced as either a batch or a continuous one.

Conventional equipment normally used by those skilled in the art can be used for the practice of this invention.

The invention is further described in the Examples which follow. All parts and percentages are by weight unless otherwise specified.

Preparation of Dimethylamine Carbamate

A one-liter flask was fitted with a dry ice condenser and a gas inlet tube. The flask was charged with 350 grams (excess) of powdered dry ice, 100 grams of dimethylamine gas was poured into the flask through the gas inlet tube over a period of about 45 minutes. The flask was allowed to reach room temperature at which time the excess of CO$_2$ vaporized. The residual liquid weighted 149.0 grams, affording a 100 percent yield of dimethylamine carbamate referred to hereinafter as DM-CARB.

The following examples illustrate general experimental procedures used for the conversion of cyclic anhydrides to diamides. Usually solid starting materials were premixed with DM-CARB in a flask until a homogeneous reaction had occurred. Then this was heated in an autoclave for the designated period of time. The reagents however, can be mixed directly in the autoclave and the reaction carried out in same vessel.

EXAMPLE 1

Preparation of N,N,N',N'-tetramethylsuccinic diamide

One hundred grams (1.0 mol) of succinic anhydride was placed into a 500 ml, three-necked flask fitted with a reflux condenser, magnetic stirrer and a dropping funnel. After nitrogen flushing 147.6 grams (1.1 mol) of DM-CARB was added drop-wise and the mixture was stirred until homogeneous. The liquid was then transferred into an autoclave and heated at 150° C./190 psi for three hours. Distillation of the reaction mixture gave the following fractions:
  (I) 8.5 grams of DM-CARB b.pt 65°–75° C./760 mm Hg
  (II) 12.3 grams of H$_2$O b.pt 45°–50° C./2.1 mm Hg
  (III) 151.0 grams of the N,N,N',N'-tetramethylsuccinic diamide 88 percent b.pt (boiling point) 156° C./0.35 mm Hg
  (IV) 6.3 grams of N,N-dimethyl succinamic acid 4.0 percent b.pt 158°–160° C./0.23 mm The NMR spectrum of fraction III in (CDCl$_3$) and tetramethylsilane (TMS) internal standard showed bands at 3.06 ppm (parts per million) (S, 6, —NC$\underline{H}$$_3$), 2.93 ppm (S, 6, —NC$\underline{H}$$_3$), and 2.63 ppm (S, 4, —(C$\underline{H}$$_2$)$_2$) thus proving the fraction consists of N,N,N',N'-tetramethyl succinic diamide.

EXAMPLE 2

Preparation of N,N,N',N'-tetramethyl diglycolic diamide

One hundred grams (0.86 mol) of diglycolic anhydride treated with 150 grams of 1.1 mol of DM-CARB as in Example 1 gave 169 grams, 90 percent yield of N,N,N',N'-tetramethyl diglycolic diamide b.pt (boiling point) 156° C./0.075 mm Hg. The nmr (nuclear magnetic resonance) spectrum in (CDCl$_3$) and TMS internal standard showed bands at 4.25 ppm (S, 4, —(C$\underline{H}$$_2$—O—C$\underline{H}$$_2$), 2.96 ppm (S, 6, —NC$\underline{H}$$_3$), and 2.90 ppm (S, 6, —NC$\underline{H}$$_3$) which are consistent with the structure of N,N,N',N'-tetramethyl diglycolic diamide.

EXAMPLE 3

Preparation of N,N,N',N'-tetramethyl maleic diamide

One hundred grams (1.01 mol) of maleic anhydride was placed into an autoclave. To this was added a small amounts of dry ice and at once 175 grams (1.3 mol) of DM-CARB. The reaction mixture was heated at 150° C. for five hours. Gas chromatography of reaction mixture indicated 85.2 percent conversion. The reaction mixture was flashed distilled with vacuum to give 51 percent yield of N,N,N',N'-tetramethyl maleic diamide. Distillation was followed by decomposition MP (melting point): 130°–131° C. from acetone. The literature melting point given by H Schindlbauer, Montsh. Chem. 99 (5) 1799 (1968) was 125°–127° C. The nmr spectrum in (CDCl$_3$) and TMS (tetramethylsilane) internal standard showed bands at 7.30 ppm (S, 2, vinyl), 3.13 ppm (S, 6, —NC$\underline{H}$$_3$), and 3.00 ppm (S, 6, —NC$\underline{H}$$_3$) which are consistent with the structure of N,N,N',N'-tetramethyl maleic diamide.

Reactions of carboxylic acids and DM-CARB were carried out directly in a rocker bomb without premixing. Two examples follow.

EXAMPLE 4

Preparation of N,N-dimethyl acetamide (DMAC)

Fifty grams (0.83 mol) of acetic acid was charged in a rocker bomb. To this was added at once 70.0 grams (0.52 mol) of DM-CARB and the mixture was heated at 150° C. for 18 hours. Excess of DM-CARB was removed in rotary evaporator. Distillation yielded the following fractions:
  (I) b.pt 74°–164° C., 22.0 grams H$_2$O
  (II) b.pt 164°–166° C., 71.9 grams DMAC (97 percent yield)

EXAMPLE 5

Preparation of N,N,N',N'-tetramethylsuccinic diamide

Fifty grams (0.42 mol) of succinic acid and 100 grams (0.75 mol) of DM-CARB were mixed directly in a rocker bomb and the mixture heated at 150° C. for 15 hours. Gas chromatography of reaction mixture indicated a 92 percent conversion. Distillation gave 48.5 grams (67.1 percent) yield of N,N,N',N'-tetramethylsuccinic diamide b.pt 115°–122° C./0.06–0.77 mm Hg.

Several of the reactions of esters and DM-CARB were carried out under atmospheric pressure. Reactions carried under pressure were mixed directly in the vessel.

EXAMPLE 6

Preparation of N,N-dimethyl-2-phenoxyacetamide

Ethyl-2-phenoxyacetate 160.0 grams (0.9 mol) was mixed with DM-CARB 536.8 grams (4 mol) and the mixture was heated with stirring to reflux under nitrogen for 18 hours. Excess DM-CARB and other volatiles were removed in rotary evaporator. Distillation of the residual liquid gave 157.0 grams (96.9 percent) of N,N-dimethyl-2-phenoxyacetamide having a boiling point of 113°–117° C./0.3–0.35 mm Hg and a MP (melting point) of 45° C. 47.5°–48.5° C. is the literature melting point given by J. Lehureau and A. Bernard, French Pat. No. 1,462,086 (1966).

EXAMPLE 7

Preparation of N,N,N',N'-tetramethylsuccinic diamide

Forty-three and one half (43.5) grams (0.25 mol) of diethylsucciniate and 67.1 grams (0.5 mol) of DM-CARB were mixed in rocker bomb and the mixture was heated at 150° C. for five hours. Reaction work-up as usual yielded 70.2 percent of N,N,N',N'-tetramethylsuccinic diamide.

EXAMPLE 8

Preparation of N,N-Dimethyl lauramide

Four (4.0) grams (0.02 mol) of lauric acid and 4.4 grams (0.033 mol) of DM-CARB were mixed in a stainless steel gas cylinder and the mixture was heated at 150° C. for 16 hours. The excess of DM-CARB was removed in a rotary evaporator. Distillation of the crude reaction product gave 4.1 grams 90 percent of N,N-dimethyl lauramide boiling point 140° C./0.60 mm Hg.

The nuclear magnetic resonance (NMR) spectrum in (CDCl$_3$) using tetramethylsilane (TMS) internal standard showed bands at 2.96 ppm (S, 3, —N—CH$_3$); 2.83 ppm (S, 3, —N—CH$_3$); 2.23 ppm (T, 2, —CH$_2$—CONMe$_2$); 1.17 ppm (M, 2, —CH$_2$); 1.26 ppm (S, 16, —(CH$_2$+$_8$) and 0.86 ppm (T, 3, CH$_3$) which are consistent with the structure for N,N-dimethyl lauramide.

EXAMPLE 9

Preparation of 2-Dodecenyl-N,N,N',N'-tetramethyl succinamide

Thirteen and three-tenths (13.3) grams (0.05 mol) of 2-dodecenylsuccinic anhydride and 13.4 grams (0.1 mol) of DM-CARB were mixed in a stainless steel gas cylinder and the mixture heated at 175° C./325 psi for 18 hours. Purification by distillation gave 12.9 grams, 76.2 percent of diamide boiling point 186° C./0.2 mm Hg NMR in CDCl$_3$ and TMS internal solvents showed bands at 5.20 ppm (M, 2, vinyl); 3.0 ppm (S, 3, —N—,—CH$_3$); 2.86 ppm (S, 3, N—CH$_3$); 2.80 ppm (S, 3, —N—CH$_3$); 2.56 ppm (S, 3, —N—CH$_3$); 1.23 ppm (S, 16, —CH$_2$) and 0.83 ppm (T, 3, —CH$_3$) which are consistent with the structure for 2-dodecenyl-N,N,N',N'-tetramethyl succinamide.

EXAMPLE 10

Preparation of N,N-Dimethyl valeramide

Twenty-six and four-tenths (26.4) grams (0.2 mol) of valeric acid treated with 20.1 grams (0.15 mol) of DM-CARB as in Example 8 gave a 95.3 percent conversion. Nuclear magnetic resonance (NMR) in CDCl$_3$ and tetramethylsilane (TMS) internal standard showed bands at 2.88 ppm (S, 3, —N—CH$_3$); 2.78 ppm (S, 3, N—CH$_3$); 2.23 ppm (M, 2, —CH$_2$—CONMe$_2$); 1.45 ppm (M, 4, —CH$_2$) and 0.93 ppm (M, 3, —CH$_3$) which are consistent with the structure for N,N-dimethyl valeramide.

EXAMPLE 11

Preparation of N,N-Dimethylformamide

Nine and two-tenths (9.2) grams (0.2 mol) of formic acid was placed into a 100 ml, three-necked flask fitted with a reflux condenser, magnetic stirrer, and a dropping funnel. After nitrogen flushing 32.6 grams (0.25 mol) of DM-CARB was added dropwise in a period of five minutes. The liquid was then transferred into a stainless steel gas cylinder and heated at 150° C. for 18 hours. The crude reaction mixture was distilled under atmospheric pressure and gave an overall of 13.0 grams, 89 percent yield of DMF having a boiling point of 155° C. 153° C./760 mm Hg is the literature boiling point given by British Pat. No. 1,519,112. NMR in polysol and TNS as internal standard showed bands of 7.96 ppm (S, 1, —COH); 3.03 ppm (S, 3, —N—CH$_3$) and 286 ppm (S, 3, —N—CH$_3$) which are consistent with the structure for N,N-dimethylformamide.

EXAMPLE 12

Preparation of N,N-Dimethylacetamide

Fifty-two (52.0) grams (0.50 mol) of malonic acid was charged to a rocker bomb. To this was added 73.8 grams (0.55 mol) of DM-CARB and the mixture was heated at 150° C. for 8 hours. Excess DM-CARB was removed in a rotary evaporator. Distillation of the crude reaction product gave 38.9 grams, 89 percent of DMAC with a boiling point of 82° C./53 mm Hg. The literature boiling point given by British Pat. No. 1,519,112 is 163° C./760 mm Hg. Nuclear magnetic resonance, neat with tetramethylsilane as internal standard showed bands at 3.0 ppm (S, 3, —N—CH$_3$), 2.91 ppm (S, 3, —N—CH$_3$), and 2.06 ppm (S, 3, CH$_3$—CO) which are consistent with the structure for N,N-dimethylacetamide.

EXAMPLE 13

Reaction of DM-CARB with Glycine

Thirty-five (35.0) grams (0.47 mol) of glycine was charged to a rocker bomb. To this was added at over 87.1 grams (0.50 mol) of DM-CARB and the mixture was heated at 200° C. for 16 hours. The excess of DM-CARB was removed in a rotary evaporator. 36.6 grams of crude material was obtained. Analysis by gas chromatography and mass spectrometry showed this to contain I. Dimethylformamide—36%
II. N,N-Dimethylacetamide—58%
III. N,N-Dimethylglycineamide—34% (M.S.: 102, 88, 60).

EXAMPLE 14

Preparation of N,N,N',N'-tetramethylfumaramide

Ninety-eight (98.0) grams (1.0 mol) of maleic anhydride was placed into a 500 ml three-necked flask fitted with a dropping funnel, magnetic stirrer, a cylindrical separatory funnel with sidearm taken off and an reflux condenser fitted on top of separatory funnel. After nitrogen flushing, 147.6 grams (1.1 mol) of DM-CARB was added dropwise and the mixture was stirred until homogeneous. The mixture was then heated at atmospheric pressure to about 90°-100° C. to remove excess DM-CARB and then to 150°-170° C. to remove water. When 18 ml of water were collected (in a period of 1 or 3 hours) the heating was discontinued and the reaction was allowed to cool to room temperature. Gas chromatography of the reaction mixture indicated 76.6 percent conversion. The product was purified by vacuum flush distillation and crystallization. From acetone yielding white crystals the melting point is 130°-131° C. The literature melting point given by British Pat. No. 1,519,112 is 125°-127° C. The nuclear magnetic resonance spectrum in CDCl$_3$ and tetramethylsilane internal standard showed bands at 7.30 ppm (S, 2, vinyl), 3.13 ppm (S, 6, —NCH$_3$) and 3.0 ppm (S, 6, —NCH$_3$) which are consistent for the structure of N,N,N',N'-tetramethylfumaramide.

EXAMPLE 15

Preparation of N,N'-Dimethyl succinamide

Four (4.0) grams (0.04 mol) of succinic anhydride was mixed with 4.4 grams (0.041 mol) of methylamine carbamate in a sealed glass tube and the mixture was heated at 150° C. for four hours. Gas chromatographic analysis of the reaction mixture indicated it contained 70 percent of N,N'-dimethylsuccinamide and 30 percent of N-methylsuccinimide. The reaction mixture washed with methylene chloride gave 4.0 grams, 69.4 percent of the diamide, melting point 173°-175° C. The literature melting point given by M. J. Hurwitz, L. S. Exnerand and P. L. DeBennenilly, J. Am. Chem Soc., 77, 3251 (1955) was 175° C. The NMR spectrum in (polysol-methanol-d$_4$) and TMS internal standard showed bands at 4.46 ppm (5, 2, —NH); 2.66 ppm (5, 6, —NH—CH$_3$);

and 2.43 ppm (5, 4, —CH$_2$—CO) confirming the gas chromatographic analysis. From the mother liquor after removing the methylene chloride in a rotary evaporator were obtained, 1.7 grams, 26.8 percent of N-methylsuccinimide.

EXAMPLE 16

Preparation of N-Methyl lauramide

Eight (8.0) grams (0.04 mol) of lauric acid was mixed with 2.7 grams (0.025 mol) of methylamine carbamate in a stainless steel cylinder and the mixture was heated at 150° C./175 psi for eight hours. Gas chromatographic analysis of the reaction mixture indicated 96.1 percent conversion to N-methyl lauramide. The NMR spectrum in (CDCl$_3$) and TMS internal standard showed bands at 2.76 ppm (D, 3, —NH—CH$_3$); 2.10 ppm (M, 2, —CH$_2$CO); 1.30 ppm (5, 10, —(CH$_2$)$_{10}$) and 0.86 ppm (M, 3, CH$_3$—) confirming the gas chromatographic analysis.

The olefin substituted succinic acid diamides prepared supra may be used as detergents, corrosion inhibitors emulsifying agents or plant growth regulators. The precursor of the amidation reaction, viz., 2-dodecenylsuccinic anhydride can be prepared by alkylation of maleic anhydride with 2-dodecene as described by Shimosaka et al. assignors to Mitsubishi Chemical Industries in Japanese Pat. No. 7,725,102.

What is claimed is:

1. Method of preparing dialkyl amides which comprises contacting an organic compound containing at least one carboxyl, carboxylic acid ester or carboxylic acid anhydride functionality with an amide carbamic acid salt having the formula:

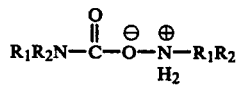

wherein each of R$_1$ and R$_2$ is a monovalent radical selected from the group consisting of —H, alkyl having 1 to about 20 carbon atoms including linear, branched and cyclic alkyls, aralkyl groups having the formula:

Ar—(CH$_2$)$_n$ wherein n is an integer having values of 1 to about 5 inclusive, Ar is an aromatic radical having up to about 15 carbons and optionally 1 hetero atom and the grouping —NR$_1$R$_2$ is a monovalent radical selected from the class consisting of piperazine, piperidine, morpholine, or pyrrole radicals, at a temperature of about 25°–250° C. until an amide is formed.

2. Method claimed in claim 1 wherein the organic compound is selected from the group consisting of
   (1) carboxylic acids having the formula

R—COOH wherein R is selected from the class consisting of H, alkyl having 1 to about 20 carbons, or —R'—COOH wherein R' is alkylene having 1 to about 18 carbons;
   (2) carboxylic acid anhydrides having the formula

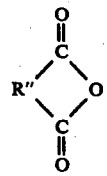

wherein R" is a divalent radical selected from the group consisting of dialkylene ether or a divalent aliphatic radical having 1 to about 20 carbons, o-phenylene or o-cyclohexylene radicals; or
   (3) carboxylic acid esters having the formula

R—COOR$_2$ wherein R is as defined above and R$_2$ is alkyl having 1 to about 8 carbons.

3. Method claimed in claim 2 wherein the organic compound has the formula

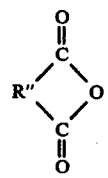

the temperature is about 100°–150° C. and the pressure is about 100–350 psi.

4. Method claimed in claim 3 wherein the organic compound is maleic anhydride.

5. Method claimed in claim 3 wherein the organic compound is succinic anhydride.

6. Method claimed in claim 3 wherein the organic compound is diglycolic anhydride.

7. Method claimed in claim 3 wherein the organic compound is 2-dodecenylsuccinic anhydride.

8. Method claimed in claim 2 wherein the organic compound has the formula

R—COOH.

9. Method claimed in claim 8 wherein the organic compound is valeric acid.

10. Method claimed in claim 8 wherein the organic compound is lauric acid.

11. Method claimed in claim 8 wherein the organic compound is glycine.

12. Method claimed in claim 8 wherein the organic compound is formic acid.

13. Method claimed in claim 8 wherein the organic compound is malonic acid.

14. Method claimed in claim 2 wherein the organic compound has the formula

R—COOR$_2$.

15. Method claimed in claim 14 wherein R is methyl and R$_2$ is ethyl.

16. Method claimed in claim 1 wherein the organic compound is ethyl-2-phenoxyacetate.

17. Method claimed in claim 1 wherein the amine carbamic acid salt is dimethyl carbamate.

18. Method claimed in claim 1 wherein the temperature is about 50° to about 200° C.

19. Method claimed in claim 1 wherein the amine carbamic acid salt is formed in situ by reacting carbon dioxide with primary or secondary amine.

* * * * *